United States Patent [19]
Boyle et al.

[11] Patent Number: 5,466,376
[45] Date of Patent: Nov. 14, 1995

[54] ON-LINE ANALYSIS FOR CONTINUOUS MEASUREMENT OF PRESENCE OF CARRYUNDER IN LIQUID-LIQUID EXTRACTION

[75] Inventors: Joseph P. Boyle; Gordon C. Camano; Randall S. Lachine; Howard R. Lingley, all of Sarnia; Raymond W. Saunders, Petrolia, all of Canada

[73] Assignee: Exxon Research & Engineering Co., Florham Park, N.J.

[21] Appl. No.: 236,906

[22] Filed: Apr. 29, 1994

[51] Int. Cl.⁶ .................................................. B01D 11/04
[52] U.S. Cl. ............................................ 210/634; 210/745
[58] Field of Search ................................. 210/634, 745, 210/742, 194, 96.1

[56] References Cited

U.S. PATENT DOCUMENTS 4,909,927  3/1990  Bell ........................................ 208/326

Primary Examiner—Frank Spear
Attorney, Agent, or Firm—Joseph J. Allocca

[57] ABSTRACT

The presence of carryunder in the extract phase recovered from a solvent extraction tower is an indication of unsatisfactory performance. The continuous analysis of the extract phase using a turbidity analyzer to detect the presence of two phases, indicating carryunder permits corrective measures to be taken in tower operation to reduce or eliminate carryunder.

4 Claims, 4 Drawing Sheets

5,466,376

ON-LINE ANALYSIS FOR CONTINUOUS MEASUREMENT OF PRESENCE OF CARRYUNDER IN LIQUID-LIQUID EXTRACTION

BACKGROUND OF THE INVENTION

1. Field of the Invention

This invention relates to controlling the performance of liquid-liquid extraction tower processes by adjusting the extraction tower operating conditions in response to the amount of carryunder present in the extract phase recovered from the extraction tower.

2. Related Art

Liquid-liquid solvent extraction is a well established process.

The separation of aromatics from hydrocarbon feed streams comprising mixtures of aromatics and non-aromatics by solvent extraction is a process which has long been practiced in the refining industry especially in the production of lubricating oil. The process involves the use of solvents such as phenol, furfural, n-methyl pyrrolidone which are selective for the aromatic components present in the hydrocarbon feed streams. The hydrocarbon stream and the selective solvents are combined, typically and preferably under countercurrent conditions. The contacting results in concentration of the aromatic component in the selective solvent. Because the solvent and the hydrocarbon oil are of different densities and generally immiscible after the contacting the aromatics rich solvent phase separates from the mixture thereby resulting in an aromatics rich solvent phase, called the extract, and an aromatics lean non-aromatics rich product phase, called the raffinate.

At certain times a portion of the distillate feed to the extractor can become entrained in the continuous extract phase leaving the bottom of the extractor. Entrainment can be caused by excessive total liquid rates (fresh feed and treat solvent) in the tower and/or inordinately high viscosities of the phases due to low temperature and low solvent water content. The tower may be operating without carryunder but after switching to a different distillate stock and adjusting operating conditions carryunder may become prevalent.

The phenomenon is similar to flooding as described in standard chemical engineering texts such as "Liquid Extraction" II Ed by Robert E. Treybal, McGraw-Hill, 1963 page 462.

The presence of carryunder in the extract constitutes loss of yield of desirable product and is a condition to be strenuously avoided. At present, extract is sampled from extraction towers on a regular but infrequent basis.

Because extractions are usually maintained at close to maximum throughput due to economic consideration to operate at maximum charge rates, any variation in feed or solvent quality or characteristic (even in a nominally constant feed or solvent profile operation) can result in the extraction process straying outside optimum limits and carryunder can be encountered.

The maximum throughput of an extractor varies with the nature of the feed charge being processed, the solvent properties (which depend on water content, temperature, pressure, and other operating condition, e.g., tower temperature profile). Unless all potential variable conditions remain constant there will be variation in the maximum throughput.

If the extractor is operating above the maximum throughput, a portion of the charge is physically entrained in the extract solution and leaves the process with the extract. In the case where the extract is the valuable product, this results in contamination of the product e.g. hexane contamination in benzene, which results in a loss valuable product.

In the case where the raffinate is the valuable product, carryunder of feed into the extract constitutes a loss in raffinate yield; that portion of the charge carried under into the extract being downgraded to extract and lost (unless extensive and expensive secondary and/or tertiary raffinate recovery steps are instituted).

If carryunder remains undetected and charge rate and/or recycle to the tower is increased, extractor flooding will occur. This process upset can last several hours even after detection and corrective measures have been taken.

Thus, the need for a fast, repeatable, accurate and continuous means for measuring for carryunder in extraction towers operation exists. It would facilitate operation of extraction tower at maximum throughput and permit more frequent changes in feed charge composition while minimizing the possible of tower operation upset.

THE PRESENT INVENTION

Figure 1:
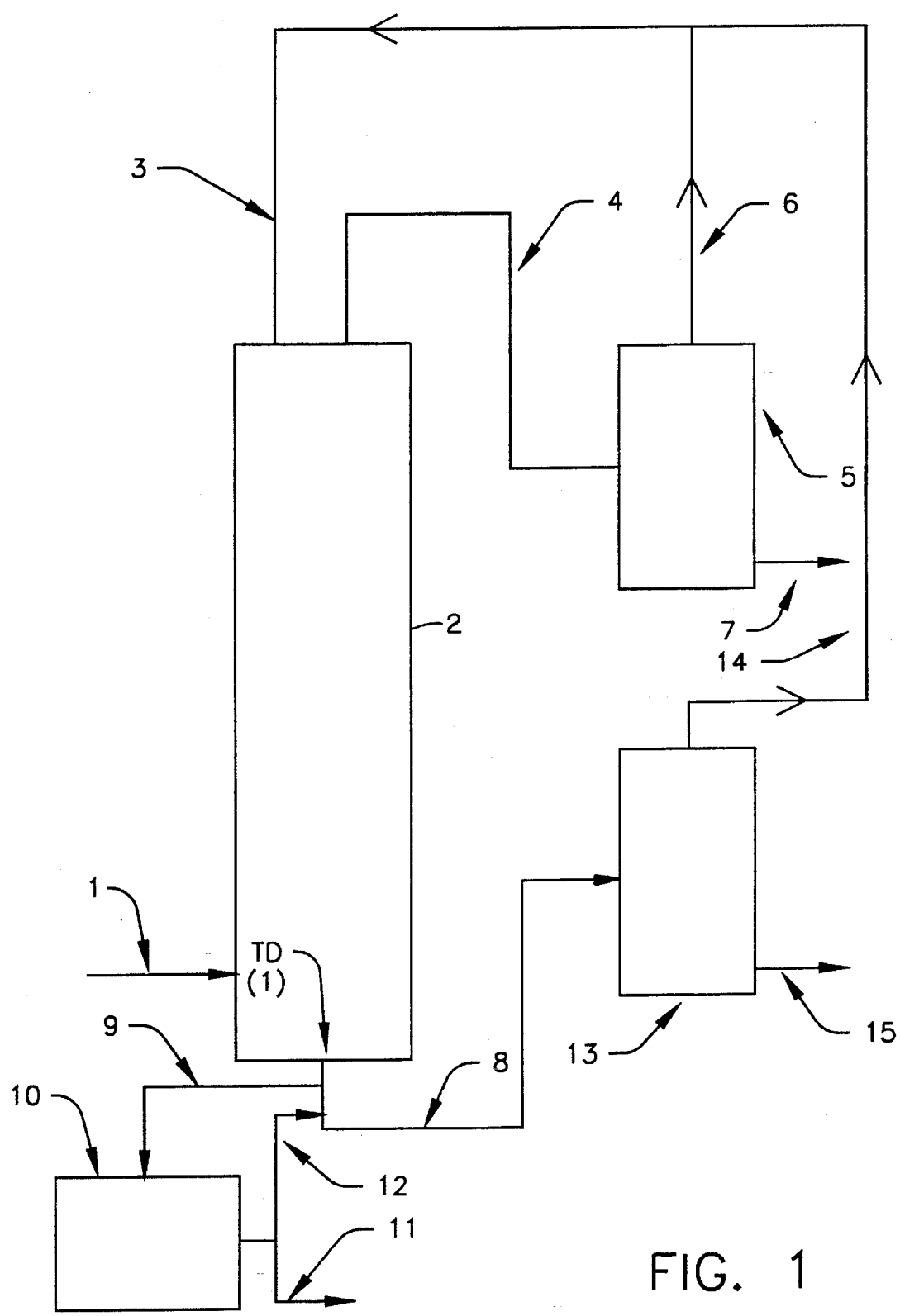
FIG. 1 is a schematic of a liquid/liquid extraction process showing the placement of the on line carryunder analyzer.

The process of the present invention comprises a method for operating an extraction tower under solvent extraction conditions comprising the steps of (a) introducing feed to be separated into components into one end of an extraction tower having a feed end and a second end, the end opposite that at which the feed is introduced being fitted with a temperature sensing means, (b) introducing a selective extraction solvent at a point opposite that at which the feed is introduced, (c) maintaining a temperature gradient the height of the tower such that the temperature at the end of the tower at which the solvent is introduced is the same or higher than the temperature at the other end of the tower the temperature at the end of the tower opposite the solvent introduction end being called the tower bottom temperature, the tower bottoms temperature, (d) recovering a raffinate from a raffinate outlet at the end of the tower at a point opposite that at which the feed was introduced, (e) recovering an extract through an extract outlet at the end of the tower at a point opposite that at which the raffinate is recovered, (f) taking a sample of extract from the extract outlet, (g) passing the extract sample through a filter to remove entrained solid particulates, (h) passing the filtered extract sample to a loop fitted with control valve means, a recirculating pump means, heating/cooling means, a temperature sensing means matched to the temperature sensing means fitted in the tower and a turbidity analyzer means, (i) closing the control valve causing the loop to become a closed recirculating loop and subjecting the filtered, extract sample circulating in the closed loop to repeated heating and cooling steps centered around the tower bottoms temperature, such heating and cooling being to temperatures about 5° to 100° F. above or below the tower bottom temperature, (j) passing the sample during the repeated heating and cooling steps through the turbidity analyzer means which analyzes for the presence of a second phase in the extract sample, the turbidity analyzer triggering a signal if a second phase is detected when the temperature of the sample is above the tower bottoms temperature thereby indicating the presence of carryunder in the extract, (k) adjusting the tower operating conditions to reduce or eliminate the carryunder, (l) flushing the extract sample from the recirculating loop, (m) repeating steps f through m.

Alternatively, a continuous slip stream may be taken from the extract, filtered, subjected to sequential heating and cooling steps, and passed through the turbidity analyzer on a once through rather than on a recirculating basis.

The solvent extraction process using the present invention may be practiced on any feed stream containing at least 2 components which can be separated by means of solvent extraction, i.e., on component is more soluble in a solvent than is the other component. Examples of such feeds includes hydrocarbon oils containing mixtures of aromatic and non-aromatic hydrocarbon. Such feeds can be separated using extraction solvents including phenol, sulfolane, furfural, $SO_2$ and n-methylpyrrolidone (NMP), preferably furfural and NMP, most preferably NMP. The NMP used may contain angrohers from 0 to 5 wt % water. The aromatic hydrocarbons are preferentially soluble in the solvent and from the extract phase.

Similarly heavy hydrocarbon fractions containing asphalt and asphaltenes can be solvent extracted using light aliphatic hydrocarbons, e.g., propane, butane, propylene, butylene (and mixtures thereof). This process is known in the art as solvent deasphalting.

In general extraction towers are expected under conditions such that a temperature gradient of from 0° to 100 ° F. exits between the end of the tower at which the solvent is introduced and the end of the tower at which the extract phase is recovered.

In the present invention, the presence of carryunder in extract in liquid-liquid extraction towers is monitored on a repetitive, high frequency basis by use of an on line turbidity analyzer. The turbidity analyzer monitors for the presence of two phases in samples of extract taken from the extraction tower as the temperature of the sample is varied above and below that which exists at the end of the extraction tower from which the sample is taken (e.g. tower bottom temperature or TBT). The observation of the existence of two phases when the sample temperature is above the tower bottom temperature is an indication that carryunder is occurring and corrective measures in tower operation can be instituted.

FIG. 1 presents a schematic of a liquid/liquid extraction process equipped with a carryunder turbidity analyzer system.

Feed charge is fed via line (1) to extraction tower (2). Solvent is fed via line (3) into the top of extraction tower (2). Raffinate phase, rich in one component of the feed charge and some solvent, is recovered via line (4) and send to raffinate recovery unit (5) wherein solvent is removed via line (6) and recycled via line (3) to the extraction tower. Solvent free raffinate is recovered via line (7). Extract phase is recovered from Tower (2) through line (8). Line (8) is fitted with a first temperature detector (TD1) which measures the tower bottom temperature. A slip stream sample is removed periodically from line (8) via line (9) and sent to analyzer system loop (10) for investigation of turbidity which relates to carryunder. Following analysis the slip stream sample is either discharged via line (11) or returned to the extract stream (8) via line (12) or discharged for disposal via line 11. Extract phase in line (8) is sent to extract recovery means (13) wherein solvent is separated from the extract phase and recycled via line (14) for combining with recovered solvent from line (6) into line (3) for introduction into the extraction tower (3). Solvent free extract is recovered via line (15).

Figure 2:
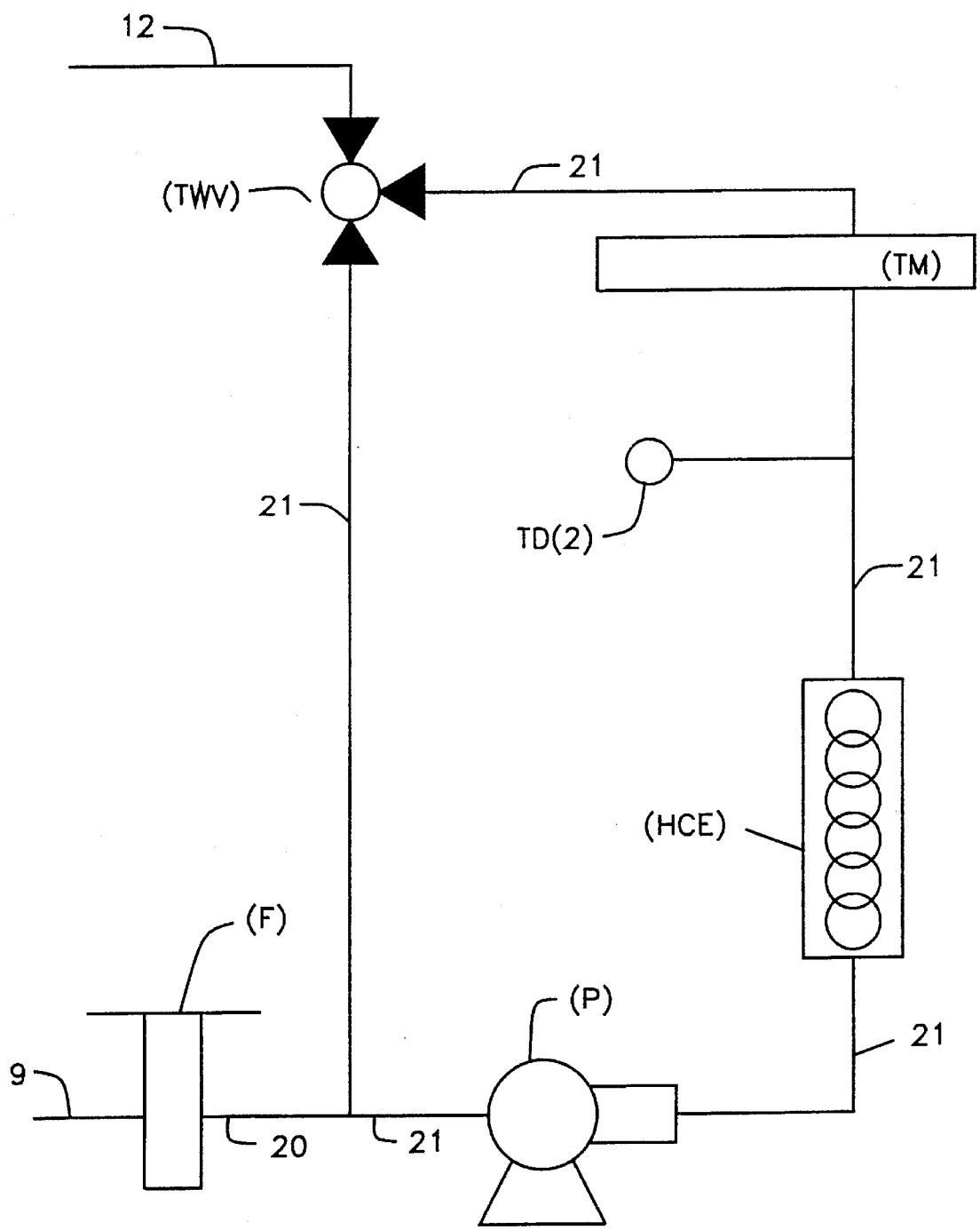
FIG. 2 is a schematic of the on-line carryunder analyzer loop.

FIG. 2 is a schematic of the analyzer system. The extract phase slip stream taken from the extract line (8) of FIG. 1 via line (9) is sent to filter (F) wherein entrained solid particulates are removed from the sample stream. The filtered sample stream is sent via line (20) to recirculating loop (21). Loop 21 is fitted with a pump (P) a heating/cooling element (HCE) a second temperature detector TD(2) (which is matched to TD(1) fitted on the extract recovery line (8) of tower (3) in FIG. 1) and a turbidity meter (TM) which analyzes for the presence of a second phase in the extract sample. The sample is subject to multiple heating/cooling cycles wherein the temperature is repeatedly raised and lowered above and below the tower bottoms temperature. Identification of a second phase in the extraction sample when the sample temperature is above the tower bottom temperature indicates the presence of carryunder in the extract. The turbidity meter can be either manually monitored or connected to an alarm to warn of carryunder. If carryunder is determined to exist corrective measures can be initiated to adjust extraction conditions in the Extraction Tower (3) of FIG. 1. Three way valve (TWV) insures that the sample is recirculated in line 21 until the heating/cooling cycles are completed and the turbidity meter has had sufficient opportunity to analyze for the presence of a second phase. Upon completion of the analysis the three way valve (TWV) is switched so that the sample is flushed from the recirculating loop (21) into e.g., line 12 for reintroduction into the extraction line (8) of FIG. 1.

Figure 3:
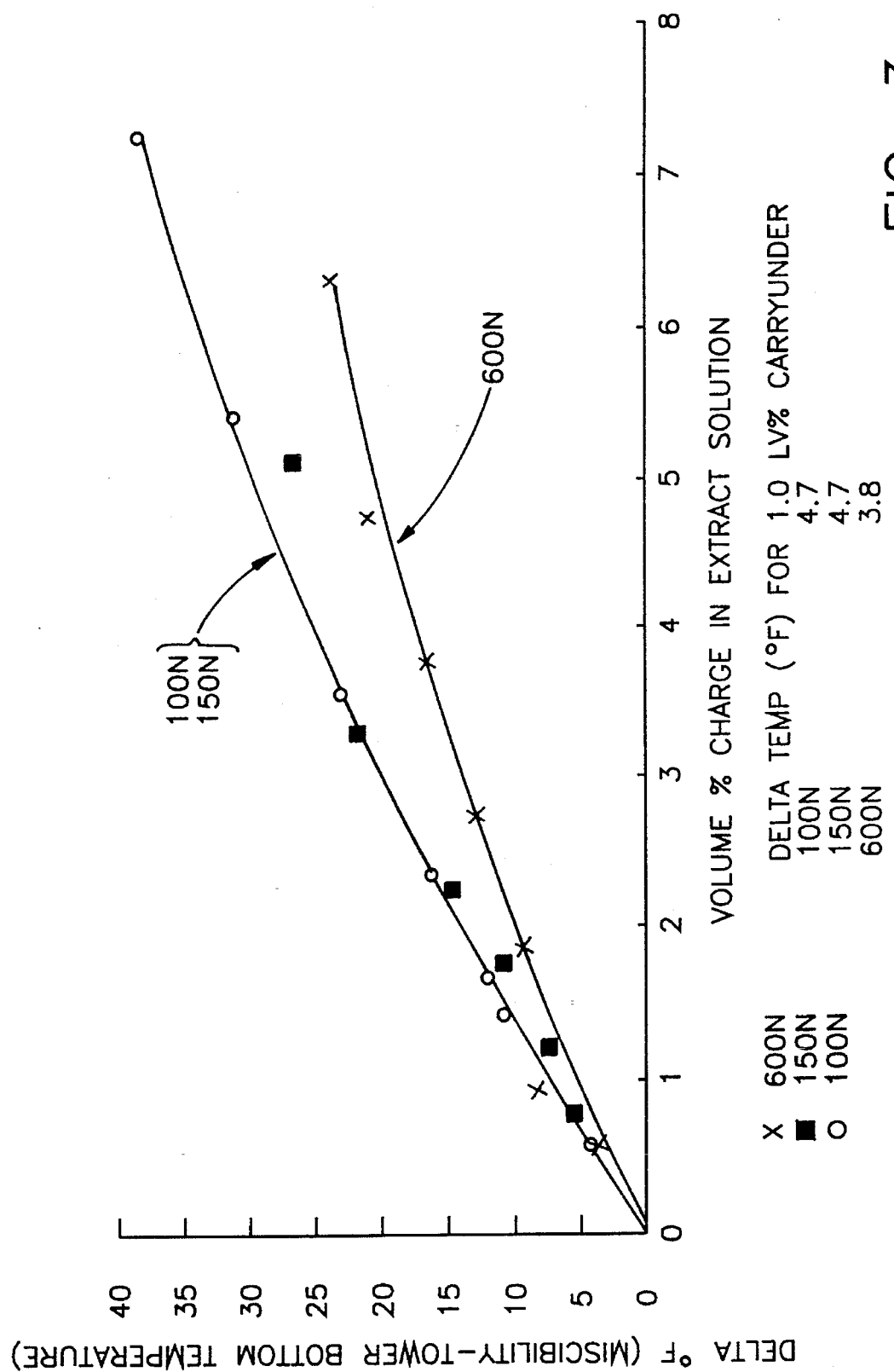
FIG. 3 shows the relationship between miscibility temperatures and volume % feed in extraction solution (e.g. miscibility temperature vs LV % carryunder).

FIG. 3 presents the relationship which exists between the miscibility temperature of the extract and the volume % feed present in the extraction solution (LV % carryunder). The Figure is for a 100, a 150 and a 600 neutral oil and shows that for those oils there is 1 LV % carryunder in the extract if there is an about +5° F. ΔT between the miscibility temperature and the tower bottom temperature. The lower bottoms temperature of the tower running on 150N oil is about 134° F.; thus if in the present invention the turbidity meter reported the presence of a two phase system at a temperature of about 140° F. (~6° F. above the TBT) the extract has about 1 LV % carryunder. If the second phase appeared at about 144°–148° F. (about 10 ° F.–14° F. above the TBT) then the extract would have about 2 LV % carryunder. Thus, based upon the ΔT above the TBT at which the second phase appear the practitioner can readily determine the approximate LV % carryunder and adjust the treat tower operating conditions (feed introduction rate, solvent introduction rate, tower temperature profile solvent water content level, solvent temperature etc.) to reduce or eliminate carryunder.

In the present invention a sample of extract is taken from the extract outlet. This sample can be taken manually or, preferably, a tap line is permanently installed into the extract outlet and samples are taken on a regular, automatic basis. The sample is filtered and introduced into a recirculation loop equipped with a pump, a heating/cooling means, a temperature detector and a turbidity detector capable of distinguishing between a one phase and a dual phase dispersed system.

The filter is used to remove entrained solids which could give a false indication of the existence of a second phase. Filters capable of removing 5–10 micron particles are preferred.

The temperature detectors used must be a matched pair so that the true temperature difference between the tower bottom temperature and the temperature at which the second phase is observed can be accurately determined. Fast response temperature detectors are needed such as resistance temperature detectors (e.g., All Temp Resistance Temperature Detector RD-S-18-10).

The turbidity meter can be any device which is capable of detecting suspended particles (solids) or the presence of a second suspend phase dispersed in a continuous phase. An example of such devices is the Monitek in line centrifuge monitor 211 turbidimeter by Monitek.

The Pump is any recirculating pump such as those produced by Micro Gear Pump (e.g. Series 5K, capacity 20 L/min. circulatory velocity 10 ft/sec. max).

The temperature detector in the loop is an identical, matched companion to a temperature detector located on the extract outlet line of the extraction tower which measures the tower bottom temperature of the extract.

The sample in the recirculation loop is subjected to at least 3 temperature changes of about 5° to 100 ° F. above and below the tower bottom temperature. A matched set of temperature measuring devices is employed, one measuring the tower bottom temperature and the other measuring the sample temperature in the recirculating loop.

The three temperature changes can be such that the temperature of the samples is first increased above the tower bottom temperature, then reduced below the tower bottom temperature then again increased above the tower bottom temperature to a temperature at least equal to and preferably above the temperature reached in the first heating.

Alternatively the sample can be first cooled, then heated then cooled.

It is preferred, however, that the sequence practiced be one of heating, cooling then heating again as this does not require the use of as extensive a cooling system nor be subject to as much delay as would be encountered if a cooling, heating, cooling sequence was employed.

The first heating is to a temperature from about 5° to 20° F. for example, a rate of from 1° to 5° F./minute, preferably 1°–2° F./minute. The sample heated to e.g. +20° F. above the tower bottoms temperature (+20° F. $\Delta T$) is maintained at that temperature for from 0 to 10 minutes to insure thorough even heating. The sample is then cooled, either by deliberate application of a cooling refrigerate under indirect cooling conditions, or, preferably simply by the cessation of heating and permitting the sample to cool under ambient conditions. The sample is cooled to from 5° to 20° F. below the tower bottom temperature at e.g., a rate of from 1° to 5° F./minute, preferably 1° F./minute. Following cooling to e.g., −20° F. below the tower bottom temperature (−20° F. $\Delta T$) the sample is again heated to from 5° to 100° F. above the tower bottom temperature (+5° to +100° F. $\Delta T$). All during this heating, cooling, heating sequence the sample is passing through the turbidity meter. If the meter detects the existence of two phases when the temperature of the sample is above the tower bottoms temperature (i.e. at a + $\Delta T$) carryunder condition exist in the extractor tower and corrective measures must be undertaken. If no second phase is detected at temperatures above the tower bottom temperature, then carryunder conditions do not exist in the extraction tower.

Upon completion of the temperature change cycle the recirculating loop is flushed (the sample therein either being discharged for disposal or preferably, recombined into the extract phase from the tower) and a fresh sample is withdrawn from the extract outlet and the process repeated. It is preferred that the sampling, and heating/cooling sequences be done automatically to increase continuous monitoring of the extract for the existence of carryunder.

It is necessary for the successful practicing of this process that the measurement of difference between the tower bottom temperature and of the sample temperature be as accurate as possible (i.e. when the extract and sample are truly at the same temperature the two measurement devices should report that they are at the same temperature, that is, report $\Delta T \equiv 0$). To this end, matched identical temperature measurement devices, regardless of type must be employed. Matching identical resistance type transduces are preferred as they have a very quick response time.

The operating principle is based on the relationship between the amount of carryunder and the difference between the tower bottom temperature and the miscibility temperature of the extract solution as determined by the suspended solids detector (turbidimeter). As shown in FIG. 3 for a 150N Western Canadian distillate, if the miscibility temperature is 140° F. and the tower bottom temperature is 135° F. then the extract solution contains about 1 LV % carryunder. For this particular feed stock, the relationship is 5°–6° F. $\Delta T$ (between miscibility and extractor bottom temperature) per 1 LV % of carryunder. While not identical, the relationship for other crudes and oil grades is of this order of magnitude so that the accuracy of determining the miscibility/tower bottom temperature difference by matching identical resistance type transducers is satisfactory.

EXAMPLE

Figure 4:
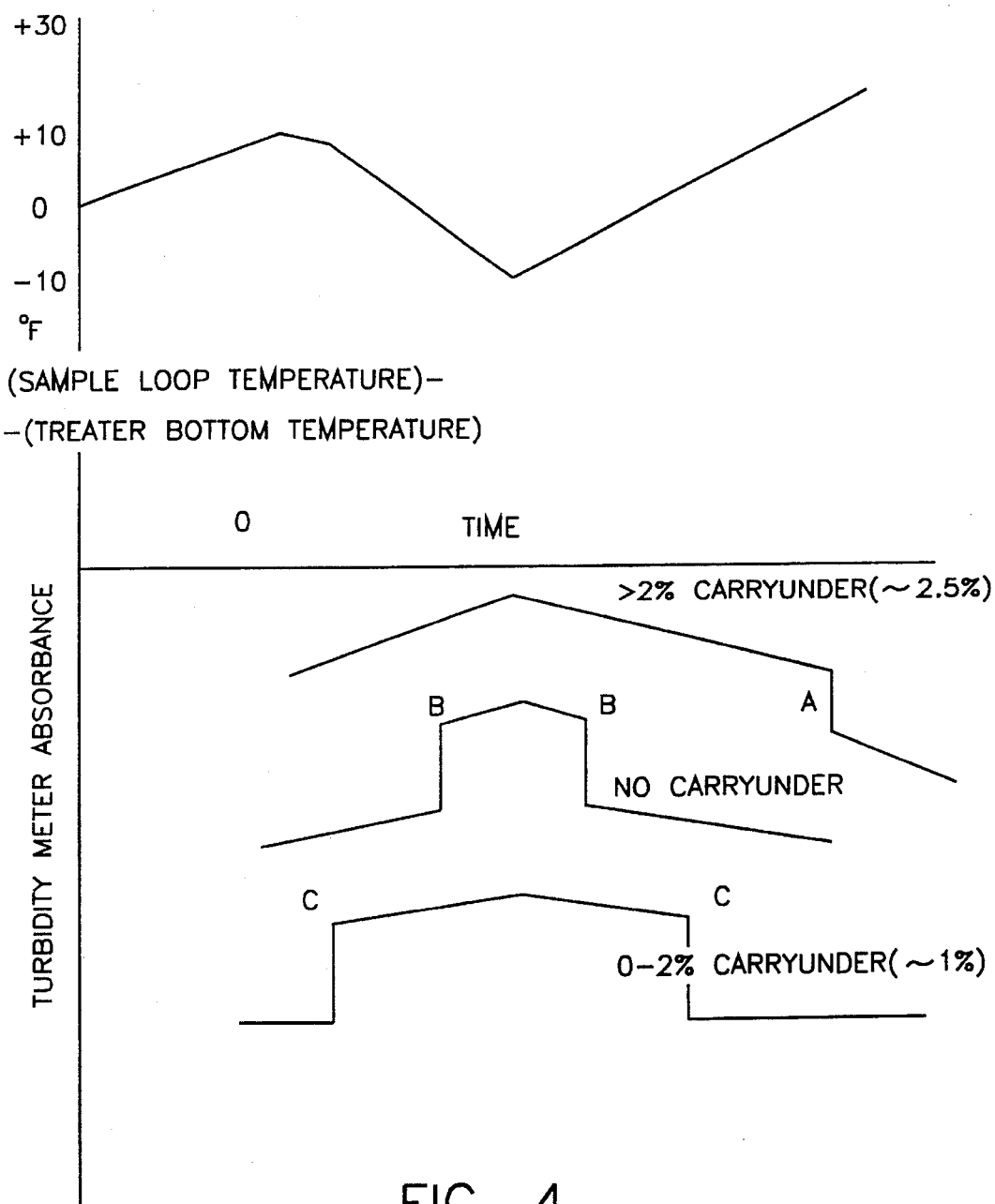
FIG. 4 shows the relationship between heating/cooling/heating cycle steps and observed turbidity for three oil samples a, b and c where sample a has about 4 LV % carryunder, b has no carryunder and c has 0–2 LV % carryunder.

A sample of extract solution produced by the extraction of a 150N oil is withdrawn from the extractor outlet, filtered then introduced into a recirculating loop. While it is circulating, the temperature is increased to TBT+10° F. Then the loop is allowed to cool through ambient heat loss to TBT−10° F. After this, the loop is heated to TBT+35° F. During the sequence the sample is passing through a turbidity meter which is analyzing for the presence of a second phase. The sample is discharged, the loop flushed and the next sample is taken. The process is repeated. Reference is made to FIG. 4.

Turbidity Meter Response

A. Carryunder >2% (~2.5% carryunder for curve A)
  Two phases will be present until miscibility is reached at a temperature of about TBT+⁻12°–14° F.
B. No Carryunder
  Sample will be miscible at TBT. Two phases will occur between TBT and TBT−10° F.
C. Carryunder <2%
  Miscibility/immiscibility transition will be detected at a temperature between TBT and TBT+10° F.

In accordance with curve A, two phases are detected until the temperature of the test sample is raised above about TBT+⁻12°–14° F. This is an indication that carryunder is present in the sample in an amount in the range of about 2+ LV %. For curve B, miscibilty change to two phase occurs at temperature below the TBT. This indicates that for the conditions under which the tower is operating there is no carryunder in the extract. Curve C indicates that miscibility change is detected at about TBT+⁻5° –6° F. Because the presence of a second phase is detected at temperatures above the TBT, this is an indication that there is carryunder in the extract. Based on FIG. 3 the detection of a second phase at TBT+⁻ 5°–6° F. for the 150N oil sample of the example is an indication that about 1 LV % carryunder is present in the extract.

What is claimed is:

1. A method for operating an extraction tower under solvent extraction conditions comprising the steps of:

(a) introducing a feed to be separated into components into one end of an extraction tower having a top end and a bottom end, the bottom being fitted with a temperature sensing means;

(b) introducing a selective extraction solvent at a point on the end of the tower opposite the end at which the feed is introduced;

(c) maintaining a temperature gradient across the height of the tower such that the temperature at the end of the tower at which the solvent is introduced is the same or higher than the temperature at the other end of the tower where the feed is introduced, the temperature at the end opposite the solvent introduction end being called the tower bottom temperature;

(d) recovering a raffinate from a raffinate outlet at a point on the end of the tower opposite the end at which the feed was introduced;

(e) recovering an extract through an extract outlet at a point on the end of the tower opposite the end at which the raffinate is recovered;

(f) taking a sample of extract from the extract outlet;

(g) passing the sample of extract through a filter to remove entrained solid particles;

(h) passing the filtered extract sample to a recirculating loop fitted with a recirculating pump means, heating/cooling means, a temperature sensing means matched to the temperature sensing means fitted in the tower and a turbidity analyzer means;

(i) subjecting the filtered, recirculating extract sample to repeated heating/cooling steps centered around the tower bottoms temperature, such heating and cooling being to temperatures about 5° to 100° F. above or below the tower bottoms temperature;

(j) passing the sample during the repeated heating and cooling steps through the turbidity analyzer means which analyzes for the presence of a second phase in the extract sample, the turbidity analyzer triggering a signal if a second phase is detected when the temperature of the sample is above the tower bottoms temperature thereby indicating the presence of carryunder in the extract;

(k) adjusting the tower operating conditions to reduce or eliminate the carryunder;

(l) opening the control valve to flush the sample from the loop;

(m) repeating steps (f) through (m).

2. A method for operating an extraction tower under solvent extraction conditions comprising the steps of:

(a) introducing a feed to be separated into components into one end of an extraction tower having a top end and a bottom end, the bottom being fitted with a temperature sensing means;

(b) introducing a selective extraction solvent at a point on the end opposite the end at which the feed is introduced;

(c) maintaining a temperature gradient across the height of the tower such that the temperature at the end of the tower at which the solvent is introduced is the same or higher than the temperature at the other end of the tower where the feed is introduced, the temperature at the end opposite the solvent introduction end being called the tower bottom temperature;

(d) recovering a raffinate from a raffinate outlet at a point on the end of the tower opposite the end at which the feed was introduced;

(e) recovering an extract through an extract outlet at a point on the end of the tower opposite the end at which the raffinate is recovered;

(f) taking a sample of extract from the extract outlet;

(g) passing the sample of extract through a filter to remove entrained solid particles;

(h) passing the filtered extract sample on a once through basis to a heating/cooling means and a temperature sensing means matched to the temperature sensing means fitted in the tower, the heating and cooling performed in the heating/cooling means being centered around the tower bottoms temperature, such heating and cooling being to temperatures about 5° to 100° C. above or below the tower bottoms temperature;

(i) passing the sample in the course of the single once through cooling/heating cycle through a turbidity analyzer means which analyzes for the presence of a second phase in the extract sample, the turbidity analyzer triggering a signal if a second phase is detected when the temperature of the sample is above the tower bottoms temperature, thereby indicating the presence of carryunder in the extract;

(j) adjusting the tower operating conditions to reduce or eliminate the carryunder;

(k) passing the sample from the heating/cooling means and the turbidity analyzer;

(l) repeating steps (f) through (l).

3. The method of claim 1 or 2 wherein the extraction process is operated under conditions such that a temperature gradient of from 0° to 100° C. exists between the end of the tower at which the solvent is introduced and the end of the tower from which the extract is recovered.

4. The method of claim 1 or 2 wherein the temperature sensing means are matched resistance temperature detectors.

* * * * *